(12) United States Patent
El-Miniawi

(10) Patent No.: US 9,023,000 B2
(45) Date of Patent: May 5, 2015

(54) ULTIMATE BIKINI UNDER PADS (UBUP)

(71) Applicant: Nasser El-Miniawi, Syosset, NY (US)

(72) Inventor: Nasser El-Miniawi, Syosset, NY (US)

(*) Notice: Subject to any disclaimer, the term of this patent is extended or adjusted under 35 U.S.C. 154(b) by 0 days.

(21) Appl. No.: 13/741,225

(22) Filed: Jan. 14, 2013

(65) Prior Publication Data
US 2014/0200528 A1 Jul. 17, 2014

(51) Int. Cl.
| | | |
|---|---|---|
| A61F 13/56 | (2006.01) | |
| A61F 13/512 | (2006.01) | |
| A61F 13/532 | (2006.01) | |
| A61F 13/84 | (2006.01) | |
| A61F 13/476 | (2006.01) | |
| A61F 13/533 | (2006.01) | |
| A61F 13/475 | (2006.01) | |
| A61F 13/511 | (2006.01) | |
| A41D 7/00 | (2006.01) | |
| A61F 13/15 | (2006.01) | |
| A61F 13/537 | (2006.01) | |

(52) U.S. Cl.
CPC ... *A61F 13/8405* (2013.01); *A61F 2013/15195* (2013.01); *A61F 13/476* (2013.01); *A61F 13/533* (2013.01); *A61F 13/475* (2013.01); *A61F 13/4756* (2013.01); *A61F 13/51108* (2013.01); *A61F 2013/53778* (2013.01); *A41D 7/00* (2013.01)

(58) Field of Classification Search
CPC ... A61F 13/00063; A61F 13/15; A61F 13/45; A61F 13/475; A61F 13/4752; A61F 13/4756; A61F 13/4757; A61F 13/49; A61F 13/49003; A61F 13/49006; A61F 13/49406; A61F 13/496; A61F 13/5605; A61F 13/565; A61F 13/82; A61F 13/84; A61F 13/8405; A61F 2013/49; A61F 2013/494; A61F 2013/49406; A61F 2013/49413; A61F 2013/8405; A61F 2013/8411; A61F 2013/4587; A61F 13/4704; A61F 13/49001; A61F 13/51108; A61F 2013/530175; A61F 2013/53765; A61F 2013/53778; A61F 2013/5378; A61F 2013/00906; A61F 2013/00646; A61F 13/4753; A61F 13/4755; A61F 13/476; A61F 13/533; A61F 2013/15195; A61M 35/00; A61M 35/006; A61M 35/003; A41D 7/00; A41D 7/005

See application file for complete search history.

(56) References Cited

U.S. PATENT DOCUMENTS

| | | | | |
|---|---|---|---|---|
| 3,897,784 | A * | 8/1975 | Fitzgerald | 604/380 |
| 3,906,952 | A * | 9/1975 | Zamist | 604/372 |
| 5,114,419 | A * | 5/1992 | Daniel et al. | 604/385.15 |
| 5,347,657 | A * | 9/1994 | Unsell | 2/67 |
| 5,388,275 | A * | 2/1995 | Oram | 2/406 |
| 5,502,842 | A * | 4/1996 | Wagner | 2/67 |

(Continued)

FOREIGN PATENT DOCUMENTS

GB    2507084 A  *  4/2014

Primary Examiner — Adam Marcetich

(57) ABSTRACT

The present Ultimate Intimate Apparel undies for woman is an intimate apparel attractive feminine hybrid design alternative that is to be disposed of after use. The lips-shaped tapered design padded area contains different layers in the innermost core, which is used as a pre-medicated with only FDA readily approved medications in a transfer medication release system, and its use treats minor feminine itching burning and irritation as it fits to the female form within the already interconnected intimate apparel undies. The article additionally has a pH balanced high waste-retaining area surrounding the medicated core and includes a feature of a water-barrier that outlines the edge of the undies, which is set as protection from seeping menses during swim, as it is used in a three-in-one all-inclusive intimate apparel.

1 Claim, 8 Drawing Sheets

(56) References Cited

U.S. PATENT DOCUMENTS

| | | | |
|---|---|---|---|
| 5,618,282 A * | 4/1997 | Schlangen | 604/387 |
| 6,482,193 B1 * | 11/2002 | Samuelsson et al. | 604/385.17 |
| 6,582,412 B2 * | 6/2003 | Christoffel et al. | 604/385.01 |
| 6,639,120 B1 * | 10/2003 | Wallajapet et al. | 604/368 |
| 6,673,982 B1 * | 1/2004 | Chen et al. | 604/378 |
| 2001/0009991 A1 * | 7/2001 | Hisanaka | 604/364 |
| 2002/0193758 A1 * | 12/2002 | Sandberg | 604/304 |
| 2003/0135172 A1 * | 7/2003 | Whitmore et al. | 604/359 |
| 2005/0182374 A1 * | 8/2005 | Zander et al. | 604/380 |
| 2009/0012489 A1 * | 1/2009 | Francoeur et al. | 604/378 |
| 2009/0065008 A1 * | 3/2009 | Clodius-Talmadge | 128/830 |
| 2010/0121296 A1 * | 5/2010 | Noda et al. | 604/367 |
| 2010/0152687 A1 * | 6/2010 | Carlozzi | 604/359 |
| 2011/0094017 A1 * | 4/2011 | Strange et al. | 2/401 |
| 2012/0289919 A1 * | 11/2012 | Van Den Bogart et al. | 604/368 |
| 2013/0018345 A1 * | 1/2013 | Van Den Bogart et al. | 604/368 |
| 2014/0107602 A1 * | 4/2014 | Hamilton | 604/359 |

* cited by examiner

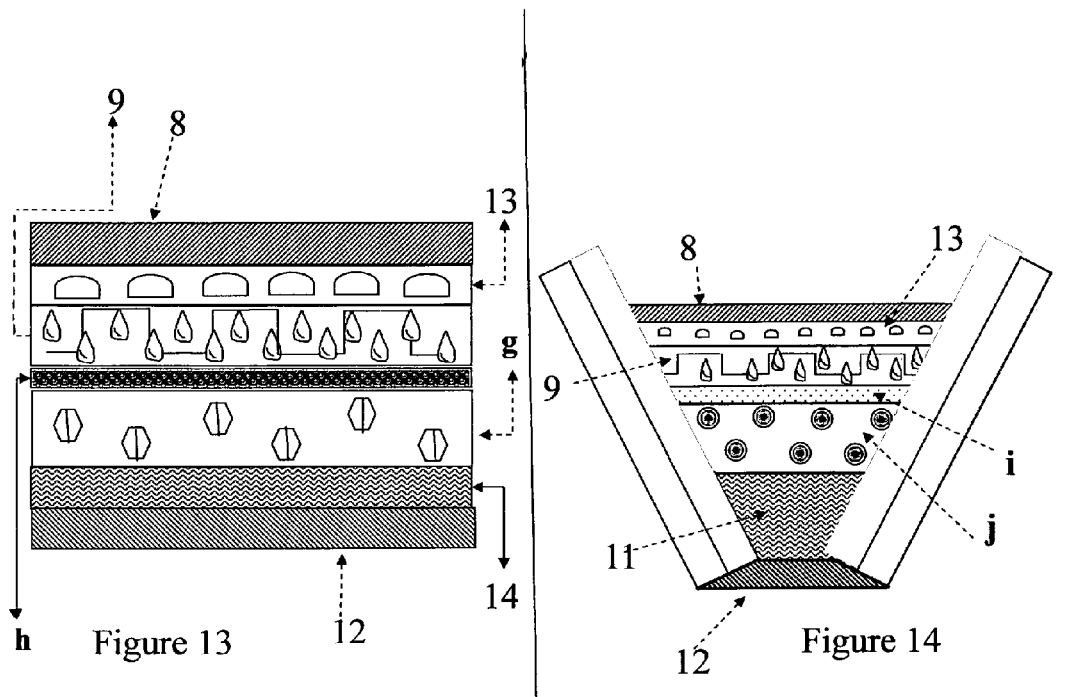
Figure 13
Figure 14
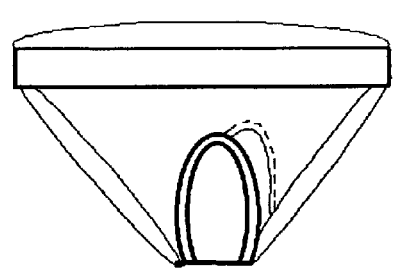
Figure 15
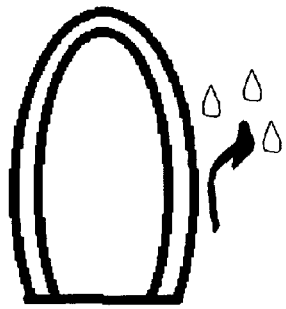
Figure 16

ULTIMATE BIKINI UNDER PADS (UBUP)

CROSS-REFERENCE TO RELATED APPLICATIONS

Not Applicable

STATEMENT REGARDING FEDERALLY SPONSORED RESEARCH OR DEVELOPMENT

Not Applicable

THE NAMES OF THE PARTIES TO A JOINT RESEARCH AGREEMENT

Not Applicable

INCORPORATION-BY-REFERENCE OF MATERIAL SUBMITTED ON A COMPACT DISC OR AS A TEXT FILE VIA THE OFFICE ELECTRONIC FILING SYSTEM (EFS-WEB)

Not Applicable

STATEMENT REGARDING PRIOR DISCLOSURES BY THE INVENTOR OR A JOINT INVENTOR

Not Applicable

BACKGROUND OF THE INVENTION (1) Technical Field

The present invention provides desirable feminine intimate apparel that contains an article that retains body waste-fluid, transfers medication, and achieves water-barrier protection, a three-in-one function.

(2) Background Art

There is a need in the art to provide a comfortable, feminine intimate apparel that can be disposed of, contains layers that can achieve maximum waste-fluid retention, that can provide medicinal treatment, and provide an enclosed compartment for swimming during menses for the pad as it is all included within an attractive intimate apparel feminine design.

BRIEF SUMMARY OF THE INVENTION

Generally, the ultimate intimate apparel tapered pad provides the attractive look as a hybrid between pads and undies (panties, underwear, swimwear etc.), with a proper lips-shape tapered design padding. The thickness of the padding and material provide quality of high retention of waste-fluid from light to heavy, including urinary incontinence.

The ultimate intimate apparel tapered pad can be scented within the lips-shape tapered design pad.

The ultimate intimate apparel tapered pad has a pre-medicated storage area, a self-treatment or pharmacist recommended FDA readily approved (only safe) medication (an anti-fungal, anti-itch, irritation relief, etc. for the vulvo-vaginal area) to prevent the need for the wearer to persistently apply a separate lotion or medication to their vulvo-vaginal area.

Physically the intimate apparel contains attractive feminine colors (possibly pink, red, black etc.) as it is included with a connected lips-shape tapered designed pad that retains waste-fluids material can be cotton, but not limited to). The lips-shape tapered design pad contains a strong, water-barrier outlining surrounding the intimate apparel under-pad. The outlining is all around the crotch area for swimming to allow women to swim freely during menses. The intimate apparel under-pad is an all-inclusive three-in-one design.

FIG L. Showing top view of the ultimate intimate apparel interior medicated storage area, and the lips-shape tapered pad area in place inside the UIAUP.

Figure 7:
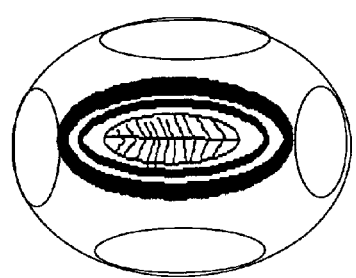
Figure 7:
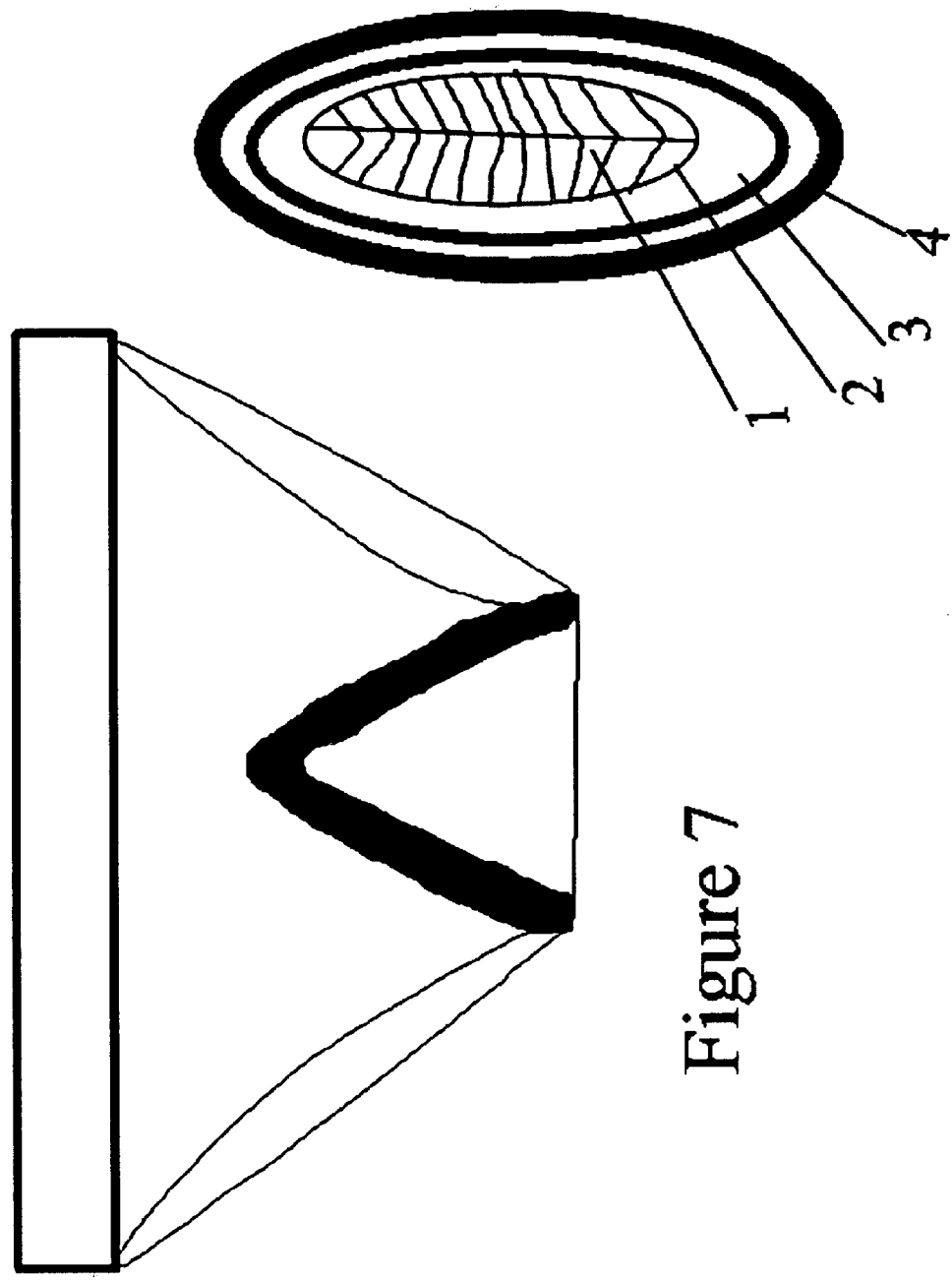

FIG. 7. Shows the different layers of medication treated pad.
  1. Inner most core concentrated area of the medication storage area containing medication transfer release system for FDA readily approved over the counter medication.
  2. Outermost side of medication storage area.
  3. Medication storage area for the female form.
  4. Outer protective barrier outlining.

Figure 8:
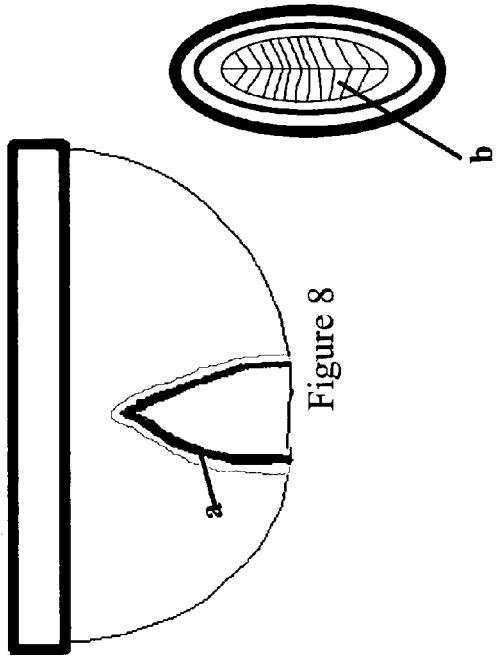

FIG. 8. Showing ½-1¼ inch outlined barrier back view [a] and 1¼×4¼ inch medication storage area interior top view [b], but can have varieties of possible size dimensions.

Figure 9:
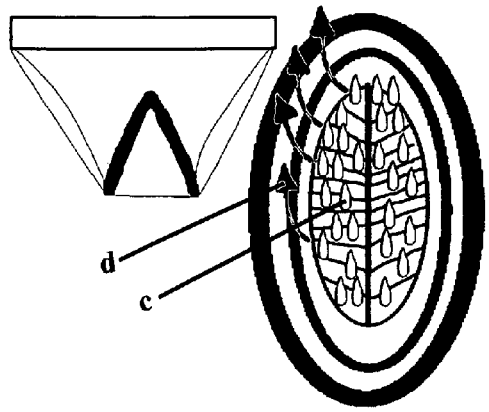

FIG. 9. Showing front view of the UIAUP, and top view of innermost medication [c], area of the transfer medication release system within The UIAUP[d].

Figure 10:
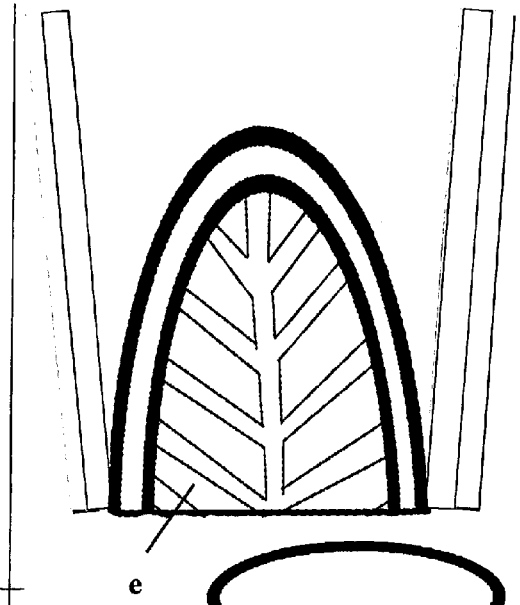

FIG. 10. Enlarged view of medication storage area with flow tunnel [e], and a protective detachable cover [f].

Figure 11:
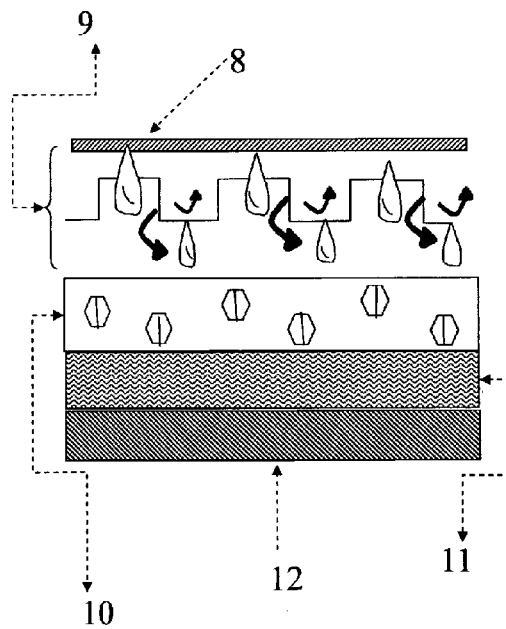
Figure 12:
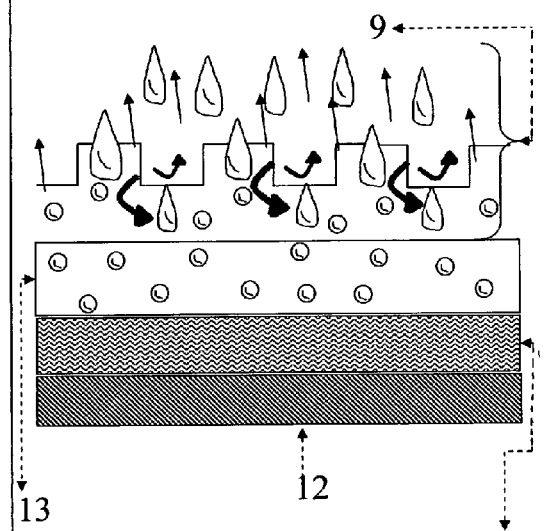

FIG. 11. Shows cross-sectional view of medicated storage area, lips-shape tapered pad area with cover.
  8. Pad cover
  9. Medication release system
  10. Medication storage area
  11. Storage area backing layer
  12. Polyethylene backing FIG. 12. Shows medication storage area in action (medication transfer release system) when pad cover is removed.

FIG. 13. Different medication order possibilities (can be, but not limited to, one layer medication only).
  g. Powder (paste)
  h. Ointment (gel)
  13. Porous layer to allow different size pores for various viscosities of medication to be able to touch the user's skin, in order to deliver active agents of various viscosities.

FIG. 14. Another different medication order possibilities (can be, but not limited to, one layer medication only).
  i. Cream (lotion)
  j. Liquid (wet wipes)

13. Porous layer to allow different size pores for various viscosities of medication to be able touch the user's skin, in order to deliver active agents of various viscosities.

FIG. 15. Three dimensional view of UIAUP.

FIG. 16. Front view of outer water-barrier outlining.

Figure 17:
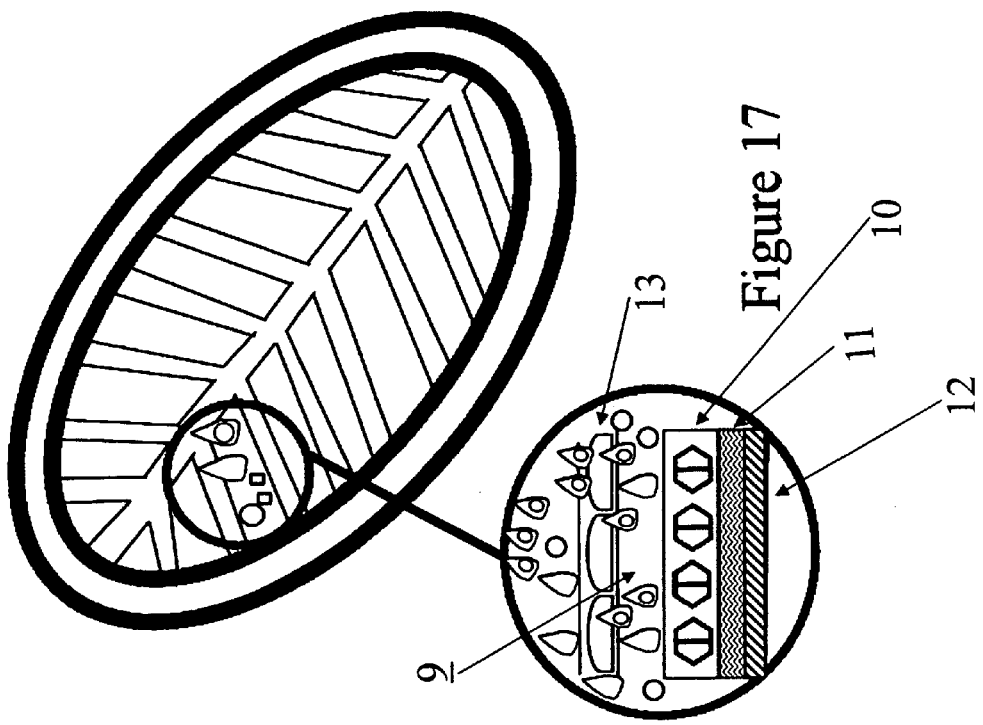

FIG. 17. Interior top view of medication transfer system, storage area. An enlargement of the lips-shape tapered area with channels that consists of medication transfer system storage area with core area.

Figure 18:
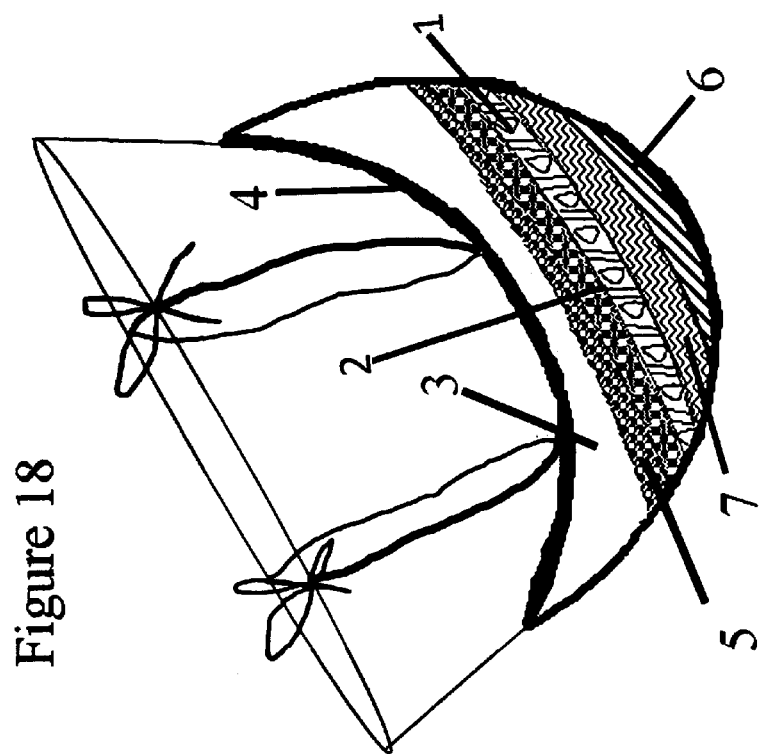

9. Medication release system
10. Medication storage area
11. Storage area backing
12. Polyethylene backing
13. Porous layer FIG. 18. Shows the cross-sectional view, in wearers, ultimate intimate apparel of the standard lips-shape tapered pad.

Layers:
1. Inner-most core of storage area.
2. Outermost side of core that retains waste-fluids (material can be cotton, but not limited to).
3. Side tunnel retaining material. Retains fluids and or leakage.
4. Outer protective water barrier outlining.
5. Top layer of retaining waste-fluids area.
6. Outer most polyethylene backing layer prevents soilage to clothing for the user common use.
7. Extra retaining waste-fluid storage outer area.

Figure 19:
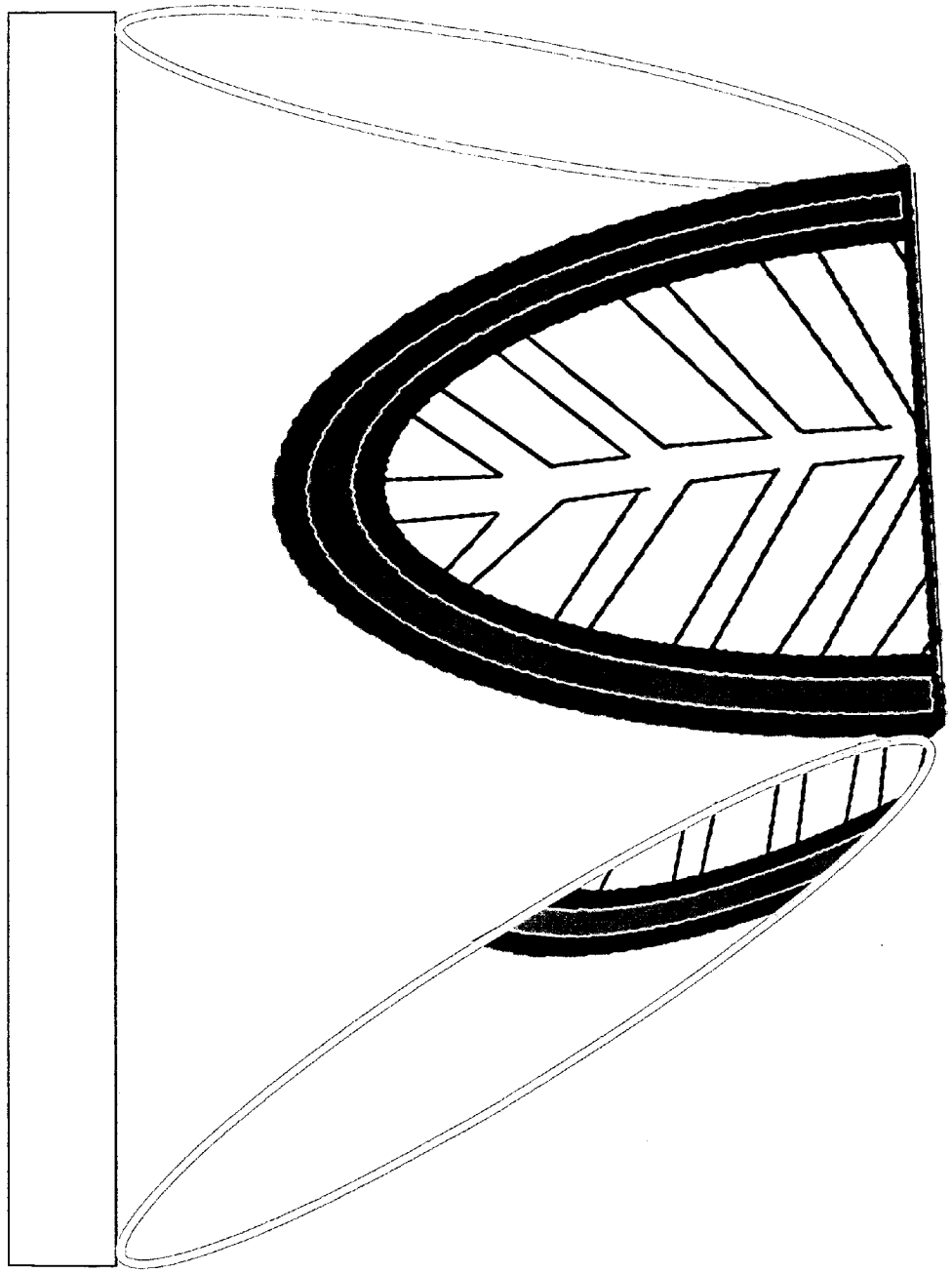

FIG. 19. Shows actual size of the ultimate intimate apparel under-pad with its lips-shape tapered pad within, but not limited to.

Figure 20:
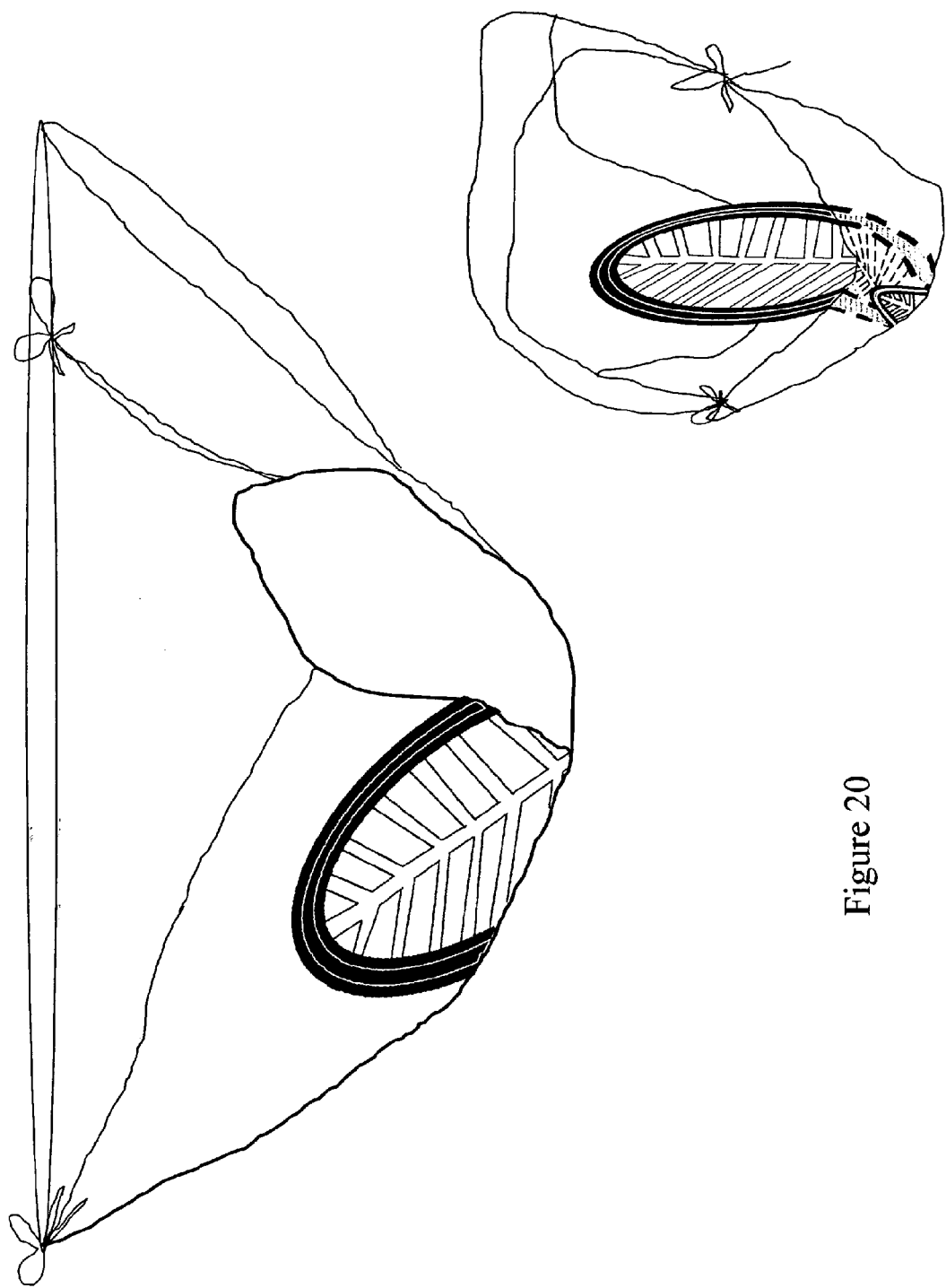

FIG. 20. Shows dimensional view of the ultimate intimate apparel and the interconnected lips-shape tapered pad top and side view as on user's body.

DETAILED DESCRIPTION OF THE INVENTION

A disposable intimate apparel under-pad that contains an intimate apparel design for feminine attraction, achieves high waste-fluid retention, helps for personal health treatment, and can be utilized during swimming. These three main points will be described in detail for the purpose of the description with reference to the accompanied drawings.

Figure 1:
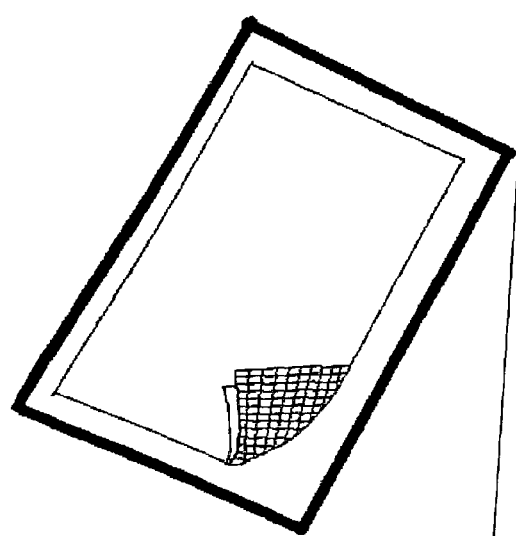
FIG. 1. Polyethylene under pad, top view, showing inner side cotton material.
Figure 2:
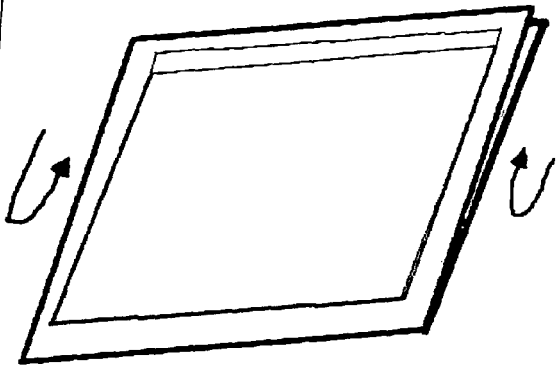
FIG. 2. Polyethylene under pad folded in half showing outer side shiny cover.
Figure 3:
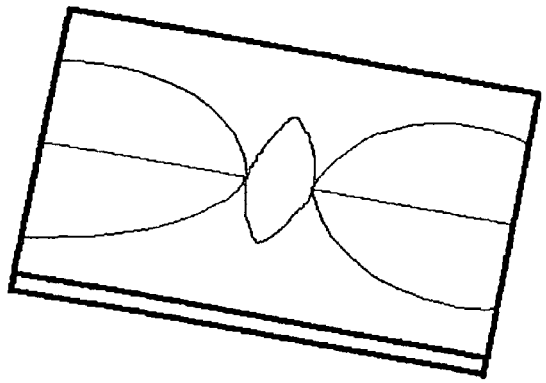
FIG. 3. Top view of the bottom (crotch) area with under pad medicated, lips-shape tapered design medication storage pad area. No seam cut pattern.
Figure 4:
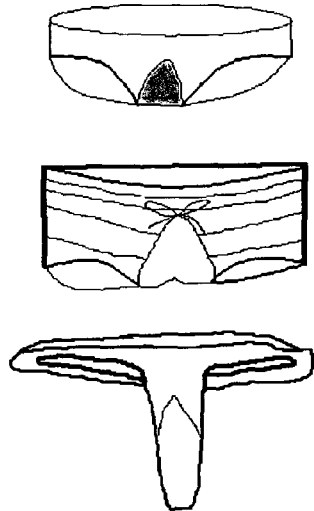
FIG. 4. Front view of the reinforced intimate apparel under-pad lips-shape tapered design of the medicated pad, as well as outer side view of intimate apparel showing design varieties.

The ultimate intimate apparel lips-shape tapered pad contains an already built and connected lips-shaped tapered pad within the intimate apparel, also shown in FIG. 4 the different intimate apparel designs. FIG. 20 is the overall view of the intimate apparel inter-connected lip-shape tapered pad shape design. In this, the tapered lips-shape medicated core in FIG. 20 contains a view of the mesh within the tapered lips-shape outer core that will help with retaining waste-fluid.

The lips-shape tapered pad has a medication transfer release system patch FIG. 17 that helps permit treatment for minor feminine itching and irritation. The storage area compartment as seen depicts an enlarged cross section of the lips-shape tapered design layers that can contain, but not limited to, four different possible forms of medicated tapered pads of the soft mesh lines medication in the intimate apparel. In detail, layer 12 is a polyethylene backing that is not permeable to said outer-side of wearer's body, layer 11 is an impermeable storage area backing, layer 10 contains a medicated storage area (which stores the medication), layer 13 is the porous layer that releases the medication of various viscosity, layer 9 is the medication release system top section of the storage area, and layer 8 is the lips-shape tapered pad cover.

The drug storage area in FIGS. 11 and 14 depicts the different forms of drug layer possibilities, but not limited to one medicated layer (layers g, h, i, j) of ointment (gel), cream (lotion), powder (paste), solution (wipes) that can be placed in the storage area. Further it could be pre-treated with, but not limited to, mineral salts for perspiration, and maintain a pH balance of a pH of 5 to 6. The storage area can have medication from simple Vaseline, Zinc, or wiping pads for minor irritation to medicated safe and other effective FDA readily approved anti-fungal, anti-itch, anti-inflammatory pre-medicated, low strength 0.5% hydrocortisone application, anesthetic 5% Benzocaine, and 2% Resorcinol, antifungal Butoconazole, Clotrimazole, Miconazole, Ticonazole cream, but not limited to, for minor vulvo-vaginal itching in the medication storage crotch lips-shaped tapered pad core area.

The ultimate intimate apparel lips shape tapered pad can be utilized for swimming during woman's menses with a water-barrier outlining as shown in FIG. 16. The outlining defines an enclosure for containing said vulvo-vaginal menses contained from said water when menses mixes with water (blood trail seepage). The lips-shape tapered pad will contain an outlining over the compartment of the lips-shape tapered pad with a cover that must be removed before swimming from the entire ultimate tapered under-pad FIG. 5, as handled in FIG. 6 to allow the water-barrier outlining to activate.

In FIG. 10 (*e*), the medicated area is at least 1¼ inch width by at least 4¼ inch length, surrounded by a high waste retention area but can have varieties of possible size dimensions depending on different female forms, of the inner core mesh. And a water-barrier outlining of ½ inch to 1¼ inch for swimming with an area that retains waste-fluid in a tunnel at thickness of at least ⅛ inch to ¼ inch in height for common use. The material is approximately at least 17 inches in length top front side to top back side (4-5 inches in front 7-9 inches on bottom 5-7 inches in back and 2½ to 3½ inches wide width crotch area). All size dimensions listed are not limited to, but are possibilities.

Figure 5:
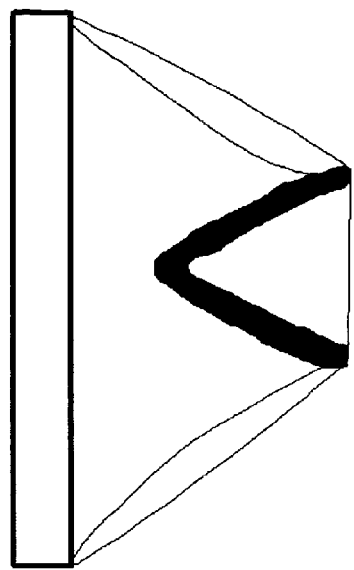
FIG. 5. Front view of the medicated intimate apparel with a view of the inside lips-shape tapered design and top view of cover for the whole lips-shape tapered design pad consisting of a water-barrier adhesive outlining, for swimming.
Figure 6:
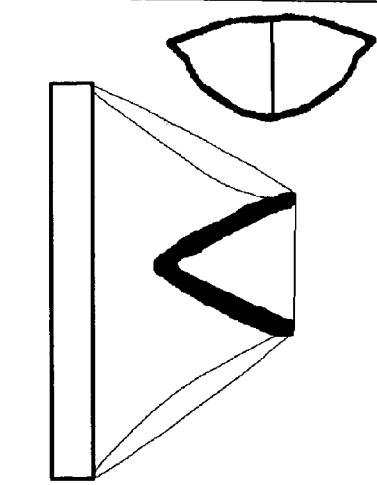
FIG. 6. Shows half the top cover sheet barrier being removed from the bottom crotch lips shape tapered pad.

Another feature of the medicated area in a natural perfumed lips-shape tapered padding with different scents, jasmine, lily, citrus, etc. The scent is secured by a pull away tapered cover and outer-lining which preserves the content until used. The outer-lining is made with a material that is intended to be thrown away or disposed of, as shown in FIG. 5.

The Ultimate intimate apparel has a lips-shaped tapered pad. Wherein the entire intimate apparel is disposable and can be thrown out after use, the intimate apparel during swim contains a water-barrier outlining that surrounds the intimate apparel and does not permit water to pass through the intimate apparel to prevent blood-trail during swim. The intimate apparel retains waste-fluid by the lips-shaped tapered pad outer core area as it prevents waste-fluid to leak out of the intimate apparel, the ultimate intimate apparel has an enclosed lips-shape tapered high waste-fluid retaining layer facing the body vulvo-vaginal area used with commercially available low cost material, the ultimate intimate apparel has an enclosed lips-shape tapered pad core with medication layer facing the vulvo-vaginal area for medicinal transfer treatment in a release system. The medicine transfer release system contains medication from the group consisting of skin anesthetics that are readily available FDA readily approved, also available, low-cost over-the-counter, azole, cortisone, hydra mine or Cain groups. The Ultimate intimate apparel has an enclosed lips-shape tapered pad medication storage area, with only readily available FDA readily approved over-the-counter medications for vulvo-vaginal treatment. The lips-shape tapered pad medication transfer treatment release system is adapted to conform to the vulvo-vaginal, a medication storage area contains medication from the group consisting of either powder, paste, lotion, cream, ointment, gel, solution, wipes, anti-fungal treatment, anti-itch treatment, anti-inflammatory treatment, anti-bacterial treatment, anesthetic treatments while maintaining a pH balance of 5 to 6 to avoid skin irritation. Wherein the lips-shaped tapered pad outer core lining has a high waste-fluid retaining and contains a feminine odor masking agent to reduce odor when retaining in waste-fluids. The ultimate intimate apparel lips shape tapered pad achieves an attractive utility for wearers featuring different feminine chroma, styles, intimate apparel, medicated, waste-retaining, and swimwear.

I claim:

1. An absorbent article configured for use during swim during menses, wherein the absorbent article comprises a pad having a sequence of layers:
   a. an absorbent transdermal layer;
   b. a medication reservoir layer;
   c. an impermeable reservoir backing layer;
   d. an impermeable outer layer;

wherein the pad comprises a convex border having two tapered corners at anterior and posterior ends;

wherein the convex border is configured to form a watertight seal to block passage of fluids between an external environment and a user's skin;

wherein the absorbent article comprises an apparel layer forming one of panties, underwear or swimwear; wherein the apparel layer is interconnected with the outer layer; and wherein the absorbent transdermal layer comprises an absorbent material having a plurality of converging channels; wherein the channels include a plurality of parallel side channels converging towards a central channel; wherein the central channel is aligned with a longitudinal axis of the absorbent article; and wherein the medication reservoir layer contains a medication selected from the group consisting of anti-fungal, anti-itch, anti-inflammatory, anti-bacterial, anesthetic or pH balancing agents.

\* \* \* \* \*